(12) United States Patent
Bestgen et al.

(10) Patent No.: US 12,338,202 B2
(45) Date of Patent: Jun. 24, 2025

(54) ONE POT SYNTHESIS OF UREA (METH)ACRYLATES

(71) Applicant: Evonik Operations GmbH, Essen (DE)

(72) Inventors: Sebastian Bestgen, Eschborn (DE); Silvia Beyer, Ober-Ramstadt (DE)

(73) Assignee: Evonik Operations GmbH, Essen (DE)

( * ) Notice: Subject to any disclaimer, the term of this patent is extended or adjusted under 35 U.S.C. 154(b) by 387 days.

(21) Appl. No.: 17/930,717

(22) Filed: Sep. 8, 2022

(65) Prior Publication Data
US 2023/0101100 A1    Mar. 30, 2023

(30) Foreign Application Priority Data
Sep. 10, 2021  (EP) .................................... 21195870

(51) Int. Cl.
*C07C 273/18* (2006.01)

(52) U.S. Cl.
CPC .... *C07C 273/1827* (2013.01); *C07C 2521/00* (2013.01); *C07C 2523/02* (2013.01); *C07C 2523/04* (2013.01); *C07C 2531/22* (2013.01)

(58) Field of Classification Search
CPC ............ C07C 2521/00; C07C 2523/02; C07C 2523/04; C07C 2531/22; C07C 2601/14; C07C 273/1827; C07C 273/1854; C07C 275/26; C07C 275/28
See application file for complete search history.

(56) References Cited

U.S. PATENT DOCUMENTS

| 4,202,990 A | 5/1980 | Murakami et al. |
| 4,672,105 A | 6/1987 | Schlosser et al. |
| 10,421,872 B1 | 9/2019 | Wendland et al. |
| 2020/0017725 A1 | 1/2020 | Lee et al. |
| 2020/0392381 A1 | 12/2020 | Qi et al. |

FOREIGN PATENT DOCUMENTS

| CN | 109879816 | 6/2019 |
| DE | 2805702 | 8/1978 |
| DE | 3423443 | 1/1986 |
| EP | 0534666 | 3/1993 |
| EP | 1534688 | 6/2005 |
| EP | 2935485 | 4/2019 |
| EP | 3643729 | 4/2020 |
| WO | 2004/016598 | 2/2004 |

OTHER PUBLICATIONS

Buruiana et al. (Preparing and structuring of block copolymers with cinnamate and adamantane, Designed Monomer and Polymers, vol. 16, No. 1, pp. 1-13, Published Jan. 2013) (Year: 2013).*
Extended European Search Report dated Apr. 7, 2022, in European Patent Application No. 21195870.7, 5 pages.
Kröhnke et al., "Antioxidants", Ullmann's Encyclopedia of Industrial Chemistry, pp. 1-36.

* cited by examiner

*Primary Examiner* — Yevgeny Valenrod
*Assistant Examiner* — Blaine G Doletski
(74) *Attorney, Agent, or Firm* — Grüneberg and Myers PLLC

(57) ABSTRACT

A one-pot synthesis of polymerizable and acyclic urea (meth)acrylates, preferably mono(meth)acrylates, can be performed via in-situ synthesis of urea alcohols or amines followed by direct reaction with a (meth)acrylate reactive diluent. The urea alcohol/amine is obtained from isocyanates and alcohols, amines, or hydroxyamines. Subsequently, the reaction with the (meth)acrylate reactive diluent takes place and the urea (meth)acrylate is directly obtained either in solution with the reactive diluent, or as a pure material after removal of the reactive diluent.

20 Claims, No Drawings

ONE POT SYNTHESIS OF UREA (METH)ACRYLATES

CROSS-REFERENCE TO RELATED APPLICATIONS

This application claims priority to European Application No. 21195870, filed on Sep. 10, 2021, the content of which is hereby incorporated by reference in its entirety.

BACKGROUND OF THE INVENTION

Field of the Invention

The present invention pertains to the one-pot synthesis of polymerizable and acyclic urea (meth)acrylates, preferably mono(meth)acrylates, via in-situ synthesis of urea alcohols or amines followed by direct reaction with a (meth)acrylate reactive diluent.

Description of Related Art

Among the vast number of polymerizable functional groups, (meth)acrylate moieties are of particular interest as they can be arbitrarily modified, additionally functionalized, exhibit beneficial safety profiles and are usually liquid or low-melting substances.

Among (meth)acrylates, polymerizable molecules bearing urea moieties are of particular interest, as the polymerizable unit ultimately enables the incorporation of urea moieties into polymeric materials. Thereby, those polymeric materials are equipped with polar, hydrophilic and hydrogen-bonding properties, which may be exploited in adhesive, coating and medicinal/biological applications.

The term "wet adhesion" is used in the paint industry to describe the ability of a paint to retain its adhesive bond to a substrate under wet or high humidity conditions. While oil-based systems are known to retain their adhesive properties under wet or humid conditions, the tendency of many water-based coatings (i.e., latexes) to lose their adhesive properties when wet has limited the usefulness of such coatings. The wet adhesion deficiency of latex paints also makes surfaces painted with such paints less scrub resistant than those surfaces painted with organic solvent-based paints.

Since the use of water-based emulsion polymer systems as protective and decorative coatings for many types of surfaces has become widespread, such systems being used by individuals in homes and in industry, there is a great need for improved wet adhesion thereof. In recent years, the art has recognized the problem of loss of adhesive properties in latex paints and a variety of modifications of such latex systems to improve wet adhesion have been proposed. Chemical incorporation of amine, amide and acetoacetate functionalities into latex polymers has been reported to improve the wet adhesion properties of latex paints. For example, a number of cyclic ureido compounds are known as imparting wet adhesion properties.

One prime and industrially most relevant example is N-(2-methacryloyloxyethyl) ethylene urea (MEEU), in which a cyclic urea moiety is linked to a methacrylate via a C2 unit. Its applications are found in polymerization and/or copolymerization processes in bulk, suspension, emulsion and solution, leading to materials which are used in the plastics, paint, leather, paper and textile industries. For many applications, it is utilized to improve wet adhesion and cohesion properties of emulsion polymers and wet scrub resistance of certain products. In its compounds, it also contributes to corrosion protection.

A slight modification of N-(2-methacryloyloxyethyl) ethylene urea is N-(2-methacrylamidoethyl) ethylene urea (N-MEEU), which simply is a methacrylamide instead of an ester. It is also used as wet adhesion monomer for latex paints and promotes adhesion of polymer resins to metal, glass, concrete and other inorganic substrates in many applications including industrial, maintenance, automotive and architectural. It improves wet adhesion effects and solvent resistance in a wide range of latex systems. It provides high adhesive power, enhanced mechanical properties and improved chemical- and water resistance to the polymer systems.

Although MEEU or N-MEEU have been developed decades ago, both monomers are still up-to-date and play a crucial role in current research activities and inventions. For coatings and adhesives, one may refer to e.g. US2020017725 (A1), EP3643729 (A1), EP2935485 (B1), U.S. Pat. No. 10,421,872 B1, or US2020392381 (A1).

However, both molecules as well as their production processes suffer from major drawbacks. First, the general synthetic procedure of the starting materials 2-hydroxyethyl ethylene urea as well as 2-aminoethyl ethylene urea is hardly modifiable and practically pretty much restricted to a five-membered cyclic urea (imidazolidin-2-one) as well as an amino/hydroxy ethyl substituent at one nitrogen atom of the imidazolidin-2-one moiety. Therefore, the range of urea containing (meth)acrylates is rather restricted to the two above mentioned molecules, known as e.g. VISIOMER® MEEU (Evonik) or SIPOMER® WAM II (Solvay). Additionally, both starting materials 2-hydroxyethyl ethylene urea as well as 2-aminoethyl ethylene urea have to be made in a separate synthetic step. Second, both products are usually obtained (and commercially distributed) as aqueous solutions or solutions in organic solvents or reactive diluents, which impedes subsequent processes in non-aqueous media (e.g. 3D printing) and applications which do not require solvents or reactive diluents. Third, N-(2-methacrylamidoethyl) ethylene urea is usually made from 2-aminoethyl ethylene urea and an activated methacrylic acid derivative (e.g. methacrylic anhydride, methacryloyl chloride), leading to the formation of often undesired and hardly removable byproducts (e.g. methacrylic acid, hydrochloric acid), which have to be laboriously separated from the product. Consequently, resolving these drawbacks is a worthwhile challenge and synthetic pathways towards anhydrous (water-free) and easily purifiable urea (meth)acrylates are still needed.

In addition, structural derivatives of the known ethylene urea ethyl (meth)acrylates/(meth)acrylamides are particularly desirable, which may ultimately lead to polymeric materials with e.g. improved (wet) adhesion and cohesion, improved anti-corrosion properties, or improved scrub resistance. This could be achieved by chemical tailoring of urea (meth)acrylates, and various synthetic routes are conceivable depending on the targeted modification.

SUMMARY OF THE INVENTION

In accordance with the above, it is an objective of the present invention to provide a new process for the preparation of new (meth)acrylate based monomers for (aqueous) emulsion polymers applied in coatings or adhesives.

As a result, the inventors have unexpectedly found that various and less polar alternative molecules to MEEU are accessible and one possible, but hardly followed alternative for the synthesis of urea functionalized (meth)acrylates or -amides lies in the synthesis of urea bearing (long-chain) alcohols or amines followed by subsequent (meth)acrylation via direct reaction (e.g. transesterification) with an (meth) acrylate reactive diluent. Unfortunately, the therefore needed urea bearing (long-chain) alcohols or amines have to be laboriously synthesized, which makes the synthesis of urea bearing (long-chain) (meth)acrylates a costly multi-step procedure. The inventors have unexpectedly found that an in situ synthesis of the urea bearing (long-chain) alcohols or amines in alkly (meth)acrylates as reactive diluent is possible, allowing for subsequent transesterification in order to obtain urea bearing (long-chain) (meth)acrylates in a one-pot procedure. The intermediate (II) is formed in situ by the reaction of an aminoalcohol or diamine of the general formula (V) with an isocyanate of the general formular (VI) in a (meth)acrylate reactive diluent of the general formula (III) in very high purity and yield, thus enabling its immediate subsequent conversion to obtain (I) in high yields and purity in a straightforward fashion.

More specifically, the present invention pertains to a one pot process for preparing (meth)acrylates of the general formula (I)

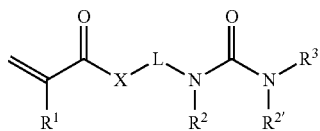

(I)

with
$R^1$ being selected from —H or -Me;
$R^2$ being selected from H, or a $C_1$-$C_{20}$ linear, branched or cyclic alkyl or aryl group;
$R^{2'}$ being —H;
$R^3$ being selected from H, or a $C_1$-$C_{20}$ linear, branched or cyclic alkyl or aryl group, as well as
benzene-sulfonyl, tosyl, p-chlorophenyl, adamantyl, 2,6-dimethyl phenyl, 3,5-dimethyl phenyl, and 2,6-dipropyl phenyl;
$R^2$ and $R^3$ being the same of different
X being selected from —O— or —NH—; and
L being selected from a $C_2$-$C_{20}$ linear, branched or cyclic alkyl or aryl group, in which optionally, one or more carbon atom within the carbon chain is replaced by one or more —O—, —NH— or —S— heteroatoms,
wherein
an intermediate compound of the general formula (II)

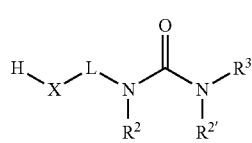

(II)

with X, $R^2$, $R^{2'}$, $R^3$, L being as defined above
is formed in situ by the reaction of an aminoalcohol or a diamine of the general formula (V)

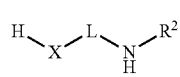

(V)

with X, $R^2$, L being as defined above
and an isocyanate of the general formula (VI)

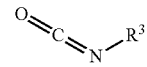

(VI)

with $R^3$ being as defined above
in the presence of a reactive diluent of the general formula (III)

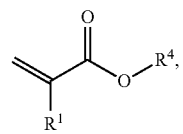

(III)

with $R^4$ being $C_1$ to $C_4$ alkyl;
wherein intermediate compound (II) is immediately reacted with reactive diluent (III), thereby forming product compound (I).

The invention also includes the following embodiments;

1. A one pot process for preparing (meth)acrylates of the general formula (I)

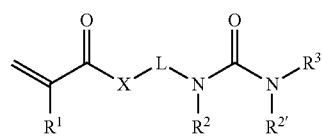

(I)

with
$R^1$ being selected from —H or -Me;
$R^2$ being selected from H, or a $C_1$-$C_{20}$ linear, branched or cyclic alkyl or aryl group;
$R^{2'}$ being —H;
$R^3$ being selected from H, or a $C_1$-$C_{20}$ linear, branched or cyclic alkyl or aryl group, as well as
benzene-sulfonyl, tosyl, p-chlorophenyl, adamantyl, 2,6-dimethyl phenyl, 3,5-dimethyl phenyl, and 2,6-dipropyl phenyl;
$R^2$ and $R^3$ being the same of different
X being selected from —O— or —NH—; and
L being selected from a $C_2$-$C_{20}$ linear, branched or cyclic alkyl or aryl group, in which optionally, one or more carbon atom within the carbon chain is replaced by one or more —O—, —NH— or —S— heteroatoms,
wherein
an intermediate compound of the general formula (II)

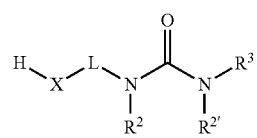

(II)

with X, $R^2$, $R^{2'}$, $R^3$, L being as defined above
is formed in situ by the reaction of an aminoalcohol or a diamine of the general formula (V)

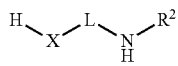
(V)

with X, $R^2$, L being as defined above
and an isocyanate of the general formula (VI)

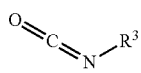
(VI)

with $R^3$ being as defined above
in the presence of a reactive diluent of the general formula (III)

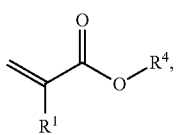
(III)

with $R^4$ being $C_1$ to $C_4$ alkyl;
wherein intermediate compound (II) is immediately reacted with reactive diluent (III), thereby forming product compound (I).

2. The process according to embodiment 1, wherein
$R^1$ is methyl.
$R^2$ is selected from hydrogen and $C_1$ to $C_8$ linear or branched alkyl,
$R^3$ is selected from methyl, ethyl, propyl, isopropyl, butyl, ethyl hexyl, cyclohexyl and phenyl,
X is oxygen; and
L is selected from ethyl, propyl, butyl, pentyl, hexyl, heptyl, octyl and ethoxyethyl.

3. The process according to any one of the preceding embodiments, wherein the process is carried out in the presence of at least one catalyst selected from the group consisting of $Zr(acac)_2$, LiOH, CaO, dioctyltin oxide (DOTO), dibutyltin laurate (DBTL), titanium isopropoxide, and combinations thereof.

4. The process according to any one of the preceding embodiments, wherein the catalyst is titanium isopropoxide or CaO/LiOH or CaO/LiCl or DOTO or DBTL.

5. The process according to any one of the preceding embodiments, wherein the catalyst is present in amounts of between 0.01 and 5 wt. %, based on the amount of compound (V).

6. The process according to any one of the preceding embodiments, wherein the reaction temperature in the initial reaction phase is kept between 0° C. and 80° C., or between 0° C. and 50° C., preferably between 0° C. and 30° C.

7. The process according to any one of the preceding embodiments, wherein the reaction temperature in the second reaction phase is kept between 30° C. and 180° C., or between 50° C. and 150° C., preferably 80° C. and 130° C.

8. The process according to any one of the preceding embodiments, wherein the reactive diluent is an alkyl (meth) acrylate selected from the group consisting of, propyl (meth) acrylate, ethyl (meth)acrylate, i-propyl (metha)crylate, i-butyl (meth)acrylate, n-butyl (meth)acrylate, and methyl (meth)acrylate.

9. The process according to any one of the preceding embodiments, wherein the reactive diluent is methyl(meth) acrylate.

10. The process according to any one of the preceding embodiments, wherein the amount of reactive diluent used is between 1 and 50, or between 2 and 20, preferably between 3 and 10 moles per mole of compound (V).

11. The process according to any one of the preceding embodiments, wherein the amount of isocyanate (VI) is 0.80 to 1.20 eq., or 0.90 to 1.10 eq., preferably 0.95 to 1.05 eq. per eq. of compound (V).

12. The process according to any one of the preceding embodiments, wherein the process is carried out in the presence of at least one polymerisation inhibitor selected from the group consisting of selected from hydrothinone monomethyl ether, 2,4-dimethyl-6-tert-butylphenol, 2,6-di-tert-butyl-4-methyl-phenol, octadecyl-3-(3,5-di-tert-butyl-4-hydroxyphenyl)-propionate, 4-hydroxy-2,2,6,6-tetramethylpiperidin-1-oxyl, and mixtures thereof.

13. The process according to embodiment 12, wherein the at least one polymerization inhibitor is hydrochinone monomethyl ether.

14. The process according to embodiment 12 or according to embodiment 13, wherein the amount of polymerization inhibitor at the beginning of the reaction is adjusted to between 0 and 5000 ppm, preferably between 100 ppm and 3000 ppm based on the amount of theoretically expected product at full conversion.

15. The process according to any one of the preceding embodiments, wherein the (meth)acrylate of the general formula (I) is obtained via precipitation, preferably wherein the at least one inhibitor is co-precipitated with the (meth) acrylate of the general formula (I).

DETAILED DESCRIPTION OF THE INVENTION

In the context of the present invention, the term (meth) acrylates includes acrylates (i.e. esters of acrylic acid) and methacrylates (i.e. esters of methacrylic acid), as well as mixtures of methacrylic acid and acrylic acid, and mixtures of acrylates and methacrylates The term "aryl" as used herein includes substituted aryl groups, and in particular alkly aryl groups, such as Ph-$CH_2$-$CH_2$-. An example for linear alkyl groups in which a carbon atom in the carbon chain is replaced by an O heteroatom is -$CH_2CH_2$-O-$CH_2CH_2$-; an example for linear alkyl groups in which a carbon atom in the carbon chain is replaced by a N heteroatom is -$CH_2CH_2$-NH-$CH_2CH_2$-.

Preferably, the (meth)acrylates of the general formula (I) are urea mono(meth)acrylates (in contrast to crosslinking di-, tri- or tetra(meth)acrylates).

In the (meth)acrylates of the general formula (I), $R^1$ is preferably methyl and $R^2$ is preferably selected from hydrogen and $C_1$ to $C_8$ linear or branched alkyl. $R^2$ being hydrogen is particularly preferred, $R^3$ is preferably selected from methyl, ethyl, propyl, isopropyl, butyl, ethyl hexyl, cyclohexyl and phenyl. $R^3$ being cyclohexyl or phenyl is particularly preferred. X is preferably oxygen; and L is preferably selected from ethyl, propyl, butyl, pentyl, hexyl, heptyl, octyl and ethoxyethyl.

Accordingly, examples for (meth)acrylates of the general formula (I) are:

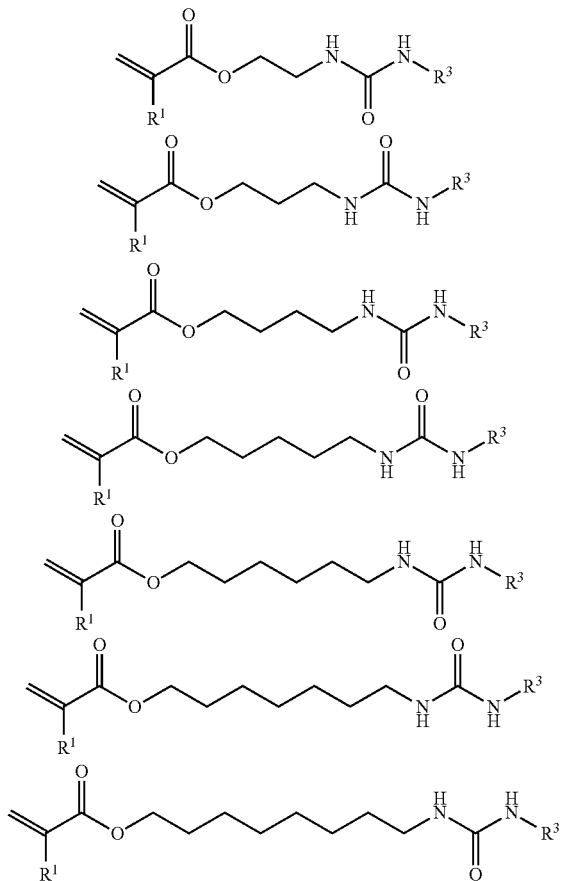

Suitable acyclic alkyl urea (meth)acrylates, in which e.g. one carbon atom is substituted with heteroatoms, such as O, NH, with linkers e.g. L=C$_5$ (C$_4$+heteroatom); R$^1$=H, Me; R$^2$=H are e.g.:

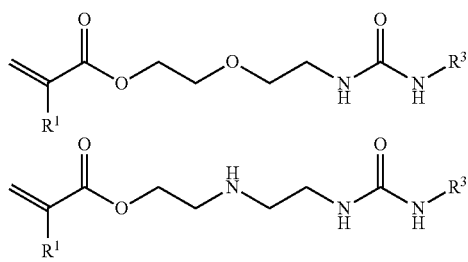

Suitable acyclic alkyl and aryl urea (meth)acrylates, with linkers e.g. L=C$_4$ and C$_6$; R$^1$=H, Me; R$^2$=H are e.g.:

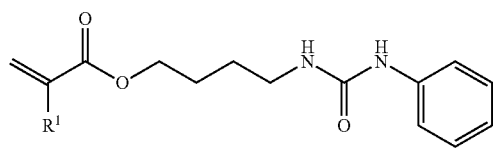

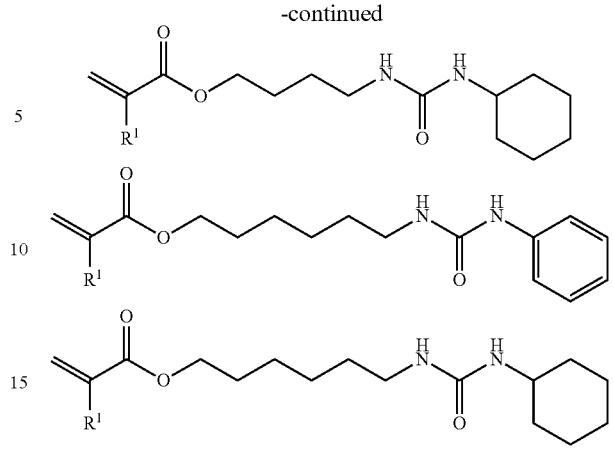

As indicated above, the intermediate urea containing alcohols and amines can be obtained in situ e.g. by the reaction of aminoalcohols or a diamines and isocyanates, such as C$_1$-C$_{30}$ monoisocyanate compounds such as benzene-sulfonyl isocyanate, tosyl isocyanate, methyl isocyanate, ethyl isocyanate, propyl isocyanate, i-propyl isocyanate, phenyl isocyanate, p-chlorophenyl isocyanate, butyl isocyanate, hexyl isocyanate, t-butyl isocyanate, cyclohexyl isocyanate, octyl iso-cyanate, 2-ethyl hexyl isocyanate, dodecyl isocyanate, adamantyl isocyanate, 2,6-dimethyl phenyl isocyanate, 3,5-dimethyl phenyl isocyanate, and 2,6-dipropyl phenyl isocyanate in the meth)acrylate species being selected from the group consisting of alkyl (meth) acrylates of the general formula (III).

The process according to the present invention thus makes the utilization of functionalized (meth)acrylate precursors such as isocyanatoethyl (meth)acrylate as well as urea-containing alcohols or amines, synthesized in a separate step, unnecessary.

The reaction with the (meth)acrylate reactive diluent as set out above is preferably carried out in the presence of at least one catalyst.

Examples for suitable catalysts are zirconium acetylacetonate and further 1,3-diketonates of zirconium, or calcium. These catalysts are disclosed in e.g. DE 28 05 702 A1.

Further examples for suitable catalysts are mixtures of alkali metal cyanates or alkali metal thiocyanates with alkali metal halides (such as LiCl); zinc compounds; alkaline earth metal oxides or alkaline earth metal hydroxides (such as CaO, Ca(OH)$_2$, MgO, Mg(OH)$_2$ or mixtures of the above compounds); alkali metal hydroxides; mixtures of alkali metal alkoxides with lithium chloride and/or lithium hydroxide; dialkyltin oxides (such as dioctyltin oxide (DOTO)), dibutyltin dilaurate (DBTL), alkali metal carbonates; alkali metal carbonates together with quaternary ammonium salts (such as tetrabutylammonium hydroxide or hexadecyltrimethylammonium bromide); mixed catalysts of diorganyltin oxide and organyltin halide; acidic ion exchangers; phosphomolybdenum heteropolyacids; titanium alcoholates such as titanium isopropoxide; chelate compounds of the metals titanium, zirconium, iron or zinc with 1,3-di-carbonyl compounds; lead compounds (such as lead oxides, lead hydroxides, lead alkoxides, lead carbonates or lead salts of carboxylic acids), amides of a metal of the first main group (such as lithium amide); or mixtures of the above-mentioned catalysts.

In addition, acids or bases can be used to catalyze the transesterification, with exemplary reaction conditions set out in the publications DE 34 23 443 and EP-A-0 534 666.

Particularly preferred catalysts for the process according to the present invention are tetraalkyl titanates such as titanium isopropoxide as well as alkaline earth metal oxides and hydroxides, such as calcium oxide and calcium hydroxide, which can be combined with alkaline metal salts such as lithium hydroxide or lithium chloride.

In accordance therewith, the process according to the present invention is advantageously carried out out in the presence of at least one catalyst selected from the group consisting of $Zr(acac)_2$, LiOH, CaO, dioctyltin oxide (DOTO), dibutyltin laurate (DBTL), titanium isopropoxide, and combinations thereof. Preferably, the catalyst is titanium isopropoxide or CaO/LiOH or CaO/LiCl or DOTO or DBTL.

[5] The catalyst may be present in amounts of between 0.01 and 5 wt. %, or between 0.1 and 3 wt. %, preferably between 0.3 to 2 wt. %, based on the amount of compound (V).

The reaction temperature in the initial reaction phase may be kept between 0° C. and 80° C., or between 0° C. and 50° C., preferably between 0° C. and 30° C., whereas the reaction temperature in the second reaction phase (transesterification phase) may be kept between 30° C. and 180° C., or between 50° C. and 150° C., very preferably 80° C. and 130° C. In this phase, the reaction mixture is advantageously heated to boiling and the alcohol $R^4OH$ which is split off is continuously distilled off with the ester, in the form of its azeotrope. Depending on the reaction temperature, the catalyst, and the catalyst amount, the reaction times range from approximately 2 to 15 hours. It is also possible to carry out the reaction in the presence of an inert solvent, for example toluene or cyclohexane, but this is normally not necessary. The reaction can take place under standard pressure, greater pressure, or in a partial vacuum.

The reactive diluent is an alkyl (meth)acrylate selected from the group consisting of, propyl (meth)acrylate, ethyl (meth)acrylate, i-propyl (metha)crylate, i-butyl (meth)acrylate, n-butyl (meth)acrylate, and methyl (meth)acrylate. Preferably, the reactive diluent is methyl(meth)acrylate. According to the above equation, equimolar amounts of the reaction partners (II) and (III) react to form the desired end products. In practice, however, it has proven to be practical to always keep the reactive diluent, i.e. the starting ester (III) in excess during the reaction. The amount of reactive diluent used may be between 1 and 50, or between 2 and 20, preferably between 3 and 10 moles per mole of compound (V).

The amount of isocyanate (VI) may be 0.80 to 1.20 eq., or 0.90 to 1.10 eq., preferably 0.95 to 1.05 eq. per eq. of compound (V).

Advantageously, the process according to the present invention is carried out in the presence of at least one polymerisation inhibitor, Within the context of the present invention, the terms "(polymerization) inhibitor" and "stabilizer" are used synonymously.

Said at least one polymerization inhibitor may be selected from the group consisting of hydroquinones, hydroquinone ethers such as hydroquinone monomethyl ether or di-tert-butylcatechol, phenothiazine, N,N'-(diphenyl)-p-phenylenediamine, 4-hydroxy-2,2,6,6-tetramethylpiperidin-1-oxyl, p-phenylenediamine, methylene blue or sterically hindered phenols, which are well known in the art. For further details, it is referred to the usual specialist literature, in particular Kröhnke, C., Schacker, O. and Zäh, M. (2015). Antioxidants, in Ullmann's Encyclopedia of Industrial Chemistry, (Ed.).

Preferably, the polymerisation inhibitor is selected from the group consisting of selected from hydrochinone monomethyl ether, 2,4-dimethyl-6-tert-butylphenol, 2,6-di-tert-butyl-4-methyl-phenol, octadecyl-3-(3,5-di-tert-butyl-4-hydroxyphenyl)-propionate, 4-hydroxy-2,2,6,6-tetramethylpiperidin-1-oxyl, and mixtures thereof. Hydrochinone monomethyl ether is particularly preferred.

The amount of polymerization inhibitor at the beginning of the reaction may be adjusted to between 0 and 5000 ppm, preferably between 100 ppm and 3000 ppm based on the amount of theoretically expected product at full conversion. Additional inhibitor may be added, preferably with an amount of additionally added stabilizer at the beginning of the reaction adjusted to between 0 and 1000 ppm based on the amount of theoretically expected product at full conversion, and most preferably with an amount of additionally added stabilizer at the beginning of the reaction adjusted to between 100 and 1000 ppm based on the amount of theoretically expected product at full conversion.

The reaction can preferably take place with stirring, the stirring speed being particularly preferably in the range from 50 to 2000 rpm, very particularly preferably in the range from 100 to 500 rpm.

The reaction can be carried out either continuously, semi-continuously or in batches. The continuous process is preferably be carried out in plants with several reactors, whereby inter alia the reaction temperature changes and alcohol or water which is released from the low-boiling (meth)acrylic acid ester can be separated from the reaction system.

Of particular interest are semi-batch processes in which part of the reaction mixture is initially charged. In further steps or continuously, after the start of the reaction, low-boiling esters of (meth) acrylic acid can be added to the reaction mixture.

The reaction is preferably carried out under an atmosphere which contains oxygen at most 20% by weight, preferably at most 10% by weight, particularly preferably at most 3% by weight. In this way, complex security measures can be avoided during the implementation, so that many cost advantages are achieved.

After completion of the reaction, excess reactive diluent (III) can be removed completely or partially, by distilling it off. The dispersed catalyst is usually removed by filtration, and it is advantageous to do so before distilling off the reactive diluent (III), which is mostly present in excess. However, it can also be removed only after partial or complete removal of excess reactive diluent (III). The catalyst, when it is recovered in the filtered form, can then be used in other alcoholysis batches, if necessary after being dried.

The thus-obtained process products of formula (I) can be used directly, i.e. without costly and qualitatively burdensome removal steps—for example as a solution in the acryl or methacryl ester—for use as comonomers, particularly in the production of dispersion polymerizates. With the above process, compounds of formula (I) can also be produced as neat liquids or solids according to the present process, for example by being evaporated from solution or by crystallization from the solvent. Preferably, the (meth)acrylate of the general formula (I) is obtained via evaporation of the reactive diluent. Alternatively, the (meth)acrylate of the general formula (I) can be obtained as solid upon cooling of the reaction mixture (after filtration, in case of heterogeneous mixtures) or via precipitation upon addition of an anti-solvent (e.g. hexane, heptane, petrol ether, etc.). The polymerization inhibitors may be co-precipitated with the product (meth)acrylates of the general formula (I), with the effect that spontaneous polymerizations in the final product can be avoided.

The monomers obtained by the process of the present invention may be used more particularly for preparing or for modifying polymers, that may be applied, for example, in binder compositions. The polymerization may take place by any known way.

Such ways include more particularly free-radical, cationic or anionic addition polymerization, it also being possible to employ variants of these addition polymerization processes, such as, for example, ATRP (atom transfer radical polymerization), NMP processes (nitroxide mediated polymerization) or RAFT (reversible addition fragmentation chain transfer).

EXAMPLES

General Synthetic Procedure for Monomers

All reactions and product manipulations were carried out in common laboratory glassware under normal conditions. Methyl (meth)acrylate, catalysts and solvents were obtained from commercial/industrial suppliers and used as received without further purification.

NMR spectra were recorded on Bruker Avance 300 or 400 spectrometers at 300 K unless otherwise noted and internally referenced to residual solvent resonances ($^1$H NMR: THF-d8: 1.72 ppm, $C_6D_6$: 7.16 ppm, toluene-d8 (tol-d8): 2.08 ppm; $CDCl_3$: 7.26 ppm. $^{13}C\{^1H\}$ NMR: THF-d8: 25.31 ppm, $C_6D_6$: 128.06 ppm, $CDCl_3$: 77.16 ppm). Chemical shifts δ are given in ppm referring to external standards of tetramethylsilane ($^1$H, $^{13}C\{^1H\}$). $^1$H and $^{13}$C NMR signals were assigned partially based on 2D NMR spectra ($^1$H, $^1$H-COSY; $^1$H, $^{13}$C-HSQC: $^1$H, $^{13}$C-HMQC).

General Procedure for the Synthesis of Intermediates (II)—Proof of Concept:

The isocyanate of the general formula (VI) (1 eq.) is mixed with the reactive diluent of the general formula (III) (e.g. methyl methacrylate), preferably cooled to 0-20° C. and stirred. Optionally, a polymerization inhibitor (e.g. MEHQ) is added. The aminoalcohol or diamine of the general formula (V) (1 eq.) is added either as pure substance or as solution in the reactive diluent of the general formula (III), so that the temperature of the reaction mixture does not exceed roughly 30° C.

Alternatively, the aminoalcohol or a diamine of the general formula (V) (1 eq.), either as pure substance or as solution in the reactive diluent of the general formula (III), is weighed into a reaction container, preferably cooled to 0-20° C. and stirred. Optionally, a polymerization inhibitor (e.g. MEHQ) is added. The isocyanate of the general formula (VI) (1 eq.) is added either as pure substance or as solution in the reactive diluent of the general formula (III), so that the temperature of the reaction mixture does not exceed roughly 30° C.

After complete addition and mixture of all components, the resulting homogeneous or heterogenous mixture is stirred for additional 30-60 minutes and brought to ambient temperature.

The intermediate (II) is obtained either as a colourless solid or oil via removal of the reactive diluent (III) under vacuum, or via filtration of the formed solid, and subsequently dried. Yields: >90%

Example 1: 1-(2-hydroxyethyl)-3-phenylurea (HEPU)

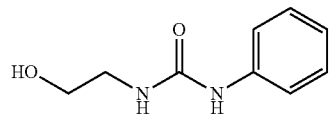 [SMILES: O=C(NCCO)Nc1ccccc1]

$^1$H NMR (DMSO-d6, 400.13 MHz): δ [ppm]=3.15 (dt, $^3$J=5.7 Hz, $^3$J=5.4 Hz, 2H, $CH_2$), 3.44 (dt, $^3$J=5.5 Hz, $^3$J=5.2 Hz, 2H, $CH_2$), 4.71 (t, $^3$J=5.2 Hz, 1H, OH), 6.15 (t, $^3$J=5.4 Hz, 1H, NH), 6.89 (tt, $^3$J=7.4 Hz, $^4$J=1.1 Hz, 1H, CH), 7.14-7.24 (m, 2H, CH), 7.32-7.41 (m, 2H, CH), 8.51 (s, 1H, NH).

$^{13}C\{^1H\}$ NMR (DMSO-d6, 100.61 MHz): δ [ppm]=41.8 ($CH_2$), 60.4 ($CH_2$), 117.6 (CH), 120.9 (CH), 128.6 (CH), 140.5 ($C_q$), 155.3 (CO).

Example 2: 1-(1-hydroxy-2-methylpropan-2-yl)-3-phenylurea

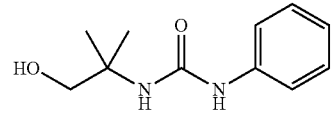

$^1$H NMR (DMSO-d6, 400.13 MHz): δ [ppm]=1.22 (s, 6H, 2×$CH_3$), 3.38 (d, $^3$J=5.6 Hz, 2H, $CH_2$), 4.96 (d, $^3$J=5.6 Hz, 1H, OH), 5.90 (bs, 1H, NH), 6.85 (tt, $^3$J=7.4 Hz, $^4$J=1.1 Hz, 1H, CH), 7.16-7.24 (m, 2H, CH), 7.31-7.36 (m, 2H, CH), 8.44 (s, 1H, NH).

$^{13}C\{^1H\}$ NMR (DMSO-d6, 100.61 MHz): δ [ppm]=23.9 ($CH_3$), 53.2 ($C(CH_3)_2$), 68.2 ($OCH_2$), 117.4 (CH), 120.8 ($CCH_2$), 128.6 (CH), 140.6 ($C_q$), 154.8 (CO).

Example 3: 1-(2-(2-hydroxyethoxy)ethyl)-3-phenylurea

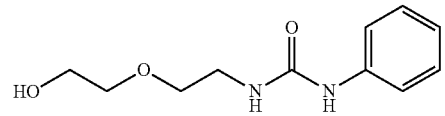 [SMILES: O=C(NCCOCCO)Nc1ccccc1]

$^1$H NMR (DMSO-d6, 400.13 MHz): δ [ppm]=3.23-3.29 (m, 2H, $CH_2$), 3.43-3.49 (m, 4H, $CH_2$), 3.50-3.56 (m, 2H, $CH_2$), 4.58 (bs, 1H, OH), 6.16 (t, $^3$J=5.6 Hz, 1H, NH), 6.88 (tt, $^3$J=7.3 Hz, $^4$J=1.2 Hz, 1H, CH), 7.16-7.25 (m, 2H, CH), 7.35-7.41 (m, 2H, CH), 8.51 (s, 1H, NH).

$^{13}C\{^1H\}$ NMR (DMSO-d6, 100.61 MHz): δ [ppm]=39.1 ($CH_2$), 60.3 ($CH_2$), 69.7 ($CH_2$), 72.1 ($CH_2$), 117.6 (CH), 121.0 (CH), 128.6 (CH), 140.5 ($C_q$), 155.2 (CO).

Example 4:
1-cyclohexyl-3-(2-(2-hydroxyethoxy)ethyl)urea

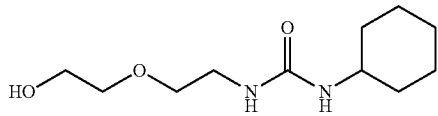 [SMILES: O=C(NCCOCCO)NC1CCCCC1]

$^1$H NMR (DMSO-d6, 400.13 MHz): δ [ppm]=0.98-1.32 (m, 5H, CH$_2$), 1.45-1.54 (m, 1H, CH$_2$), 1.56-1.66 (m, 2H, CH$_2$), 1.67-1.78 (m, 2H, CH$_2$), 3.08-3.16 (m, 2H, NHCH$_2$), 3.32-3.44 (m, 5H, NHCH and CH$_2$), 3.45-3.52 (m, 2H, CH$_2$), 4.54 (t, $^3$J=5.5 Hz, 1H, OH), 5.72 (t, $^3$J=5.6 Hz, 1H, NH), 5.81 (d, $^3$J=8.2 Hz, 1H, NH).

$^{13}$C{$^1$H} NMR (DMSO-d6, 100.61 MHz): δ [ppm]=24.4 (CH$_2$), 25.3 (CH$_2$), 33.3 (CH$_2$), 39.2 (NHCH$_2$), 47.7 (NHCH), 60.2 (CH$_2$OH), 70.1 (OCH$_2$), 72.1 (OCH$_2$), 157.3 (CO).

Example 5: 1-(6-hydroxyhexyl)-3-phenylurea

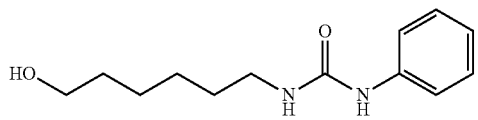 [SMILES: O=C(NCCCCCCO)Nc1ccccc1]

$^1$H NMR (DMSO-d6, 400.13 MHz): δ [ppm]=1.23-1.34 (m, 4H, CH$_2$), 1.36-1.48 (m, 4H, CH$_2$), 3.06 (dt, $^3$J=6.7 Hz, $^3$J=5.7 Hz, 2H, CH$_2$), 3.39 (dt, $^3$J=6.4 Hz, $^3$J=5.3 Hz, 2H, CH$_2$), 4.31 (t, $^3$J=5.3 Hz, 1H, OH), 6.07 (t, $^3$J=5.7 Hz, 1H, NH), 6.87 (tt, $^3$J=7.3 Hz, $^4$J=1.1 Hz, 1H, CH), 7.17-7.23 (m, 2H, CH), 7.33-7.40 (m, 2H, CH), 8.33 (s, 1H, NH).

$^{13}$C{$^1$H} NMR (DMSO-d6, 100.61 MHz): δ [ppm]=25.3 (CH$_2$), 26.3 (CH$_2$), 29.8 (CH$_2$), 32.5 (CH$_2$), 39.0 (CH$_2$), 60.6 (CH$_2$), 117.5 (CH), 120.8 (CH), 128.6 (CH), 140.6 (C$_q$), 155.2 (CO)

Example 6: 1-cyclohexyl-3-(6-hydroxyhexyl)urea

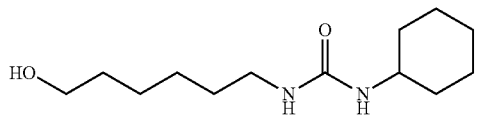 [SMILES: O=C(NCCCCCCO)NC1CCCCC1]

$^1$H NMR (DMSO-d6, 400.13 MHz): δ [ppm]=0.96-1.17 (m, 3H, CH$_2$), 1.28-1.45 (m, 10H, CH$_2$), 1.46-1.55 (m, 1H, CH$_2$), 1.56-1.67 (m, 2H, CH$_2$), 1.67-1.77 (m, 2H, CH$_2$), 2.94 (dt, $^3$J=6.7 Hz, $^3$J=6.3 Hz, 2H, CH$_2$), 3.25-3.41 (m, 3H, overlapping CH & CH$_2$), 4.30 (bs, 1H, OH), 5.58-5.66 (m, 2H, NH).

$^{13}$C{$^1$H} NMR (DMSO-d6, 100.61 MHz): δ [ppm]=24.4 (CH$_2$), 25.2 (CH$_2$), 25.3 (CH$_2$), 26.3 (CH$_2$), 30.0 (CH$_2$), 32.5 (CH$_2$), 33.3 (CH$_2$), 39.1 (CH$_2$), 47.6 (CH), 60.6 (CH$_2$), 157.4 (CO).

General Procedure for the Synthesis of Monomers (I)

The isocyanate of the general formula (VI) (1 eq.) is mixed with the reactive diluent of the general formula (Ill) (e.g. methyl methacrylate), preferably cooled to 0-20° C. and stirred. Optionally, a polymerization inhibitor (e.g. MEHQ) is added. The aminoalcohol or diamine of the general formula (V) (1 eq.) is added either as pure substance or as solution in the reactive diluent of the general formula (III), so that the temperature of the reaction mixture does not exceed roughly 30° C.

Alternatively, the aminoalcohol or diamine of the general formula (V) (1 eq.), either as pure substance or as solution in the reactive diluent of the general formula (III), is weighed into a reaction container, preferably cooled to 0-20° C. and stirred. Optionally, a polymerization inhibitor (e.g. MEHQ) is added. The isocyanate of the general formula (VI) (1 eq.) is added either as pure substance or as solution in the reactive diluent of the general formula (III), so that the temperature of the reaction mixture does not exceed roughly 30° C.

After complete addition and mixture of all components, the resulting homogeneous or heterogenous mixture is stirred for additional 30-60 minutes and brought to ambient temperature. Additional inhibitors may be added.

In a reactor with mechanical stirring, air supply, sump temperature display, a filling element column set on it, as well as an automatically controlled column head with reflux and distillate cooler, the mixture is then heated to boiling and for the reactive diluent (III)=methyl methacrylate, first a methyl methacrylate-water azeotrope is distilled off, until no more azeotrope distillate and instead pure methyl methacrylate distillate is observed (in case anhydrous starting materials are used, this removal-of-water-step via azeotrope-distillation is not necessary). The batch is cooled by about 10-20° C., and a catalyst (e.g. titanium isopropoxide (IPT)) (1% rel. to intermediate urea-containing alcohol or amine (II)) as well as methyl methacrylate, the amount being equivalent to the mass of the lost azeotrope distillate, are added.

Again, the mixture is heated to boiling, and the resulting methyl methacrylate-methanol azeotrope is distilled off at a reflux ratio of 2:1, up to a maximum head temperature of 70° C., and later at a reflux ratio of 10:1, until a constant column head temperature of 98-101° C. is reached. The reaction is typically terminated within 2 h-16 h. The batch is cooled to 80° C. When titanium alkoxides have been used as catalyst, diluted sulfuric acid followed by sodium carbonate is added. Optionally Tonsil or Celatom or Celite are added. The batch is filtered by pressure filtration (EKS pressure filter). The clear filtrate is optionally obtained as a solution in methyl methacrylate or concentrated under vacuum (RT to 125° C., ambient pressure or up to 1 mbar) until the product is obtained as a colourless oil or solid. Optionally, the product may be obtained as crystalline material upon cooling of the solution. Optionally, the product may be recrystallized from suitable common organic solvents, such as e.g. ethyl acetate, methanol, ethanol and acetone. Optionally, the product may be washed with suitable organic solvents, such as e.g. pentane, hexane, heptane, diethyl ether or toluene.

Example 1: Synthesis of 2-(3-phenylureido)ethyl methacrylate

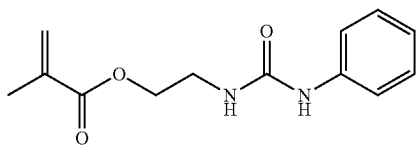 [SMILES: C=C(C)C(=O)OCCNC(=O)Nc1ccccc1]

Phenyl isocyanate (49.3 g, 0.414 mol, 1.00 eq.) is dissolved in methyl methacrylate (331 g, 3.31 mol, 8.00 eq.). MEHQ (44 mg, 200 ppm based on product) is added. The temperature of the mixture is kept below 20° C., and ethanolamine (25.53 g, 0.418 mol, 1.01 eq.) is added dropwise over 15 minutes. The heterogeneous mixture is further diluted with methyl methacrylate (84.6 g, 0.84 mol, 2.00 eq.), brought to room temperature and heated to 100° C. to remove any water as water-methyl methacrylate azeotrope. The mixture is cooled to 80° C., and the catalyst (e.g. IPT (1% based on urea alcohol) or Zr(acac)2 (1% based on urea alcohol) or LiOH (1% based on urea alcohol) is added. The mixture is heated to 120° C. and methanol-methyl methacrylate is gradually azeotropically removed (with adjusted reflux ratio) until complete conversion is obtained after 6 hours. Optionally, the pure product can be obtained as crystalline solid upon cooling of the reaction mixture. Typically, the catalyst is either directly removed by filtration of the reaction solution (over e.g. Celite, Celatome, Arbocell) or, in case of IPT, precipitated first with diluted sulfuric acid, and then removed by filtration of the reaction solution (over e.g. Celite, Celatome, Arbocell).

$^1$H NMR (DMSO-d6, 400.13 MHz): δ [ppm]=1.89 (dd, $^4$J=1.5 Hz, $^4$J=1.0 Hz, 3H, CH$_3$), 3.39 (dt, $^3$J=5.5 Hz, $^3$J=5.8 Hz, 2H, CH$_2$), 4.14 (t, $^3$J=5.5 Hz, 2H, CH$_2$), 5.68 (dq, $^4$J=1.5 Hz, $^4$J=1.1 Hz, 1H, CH$_2$), 6.08 (bs, 1H, CH$_2$), 6.26 (t, $^3$J=5.8 Hz, 1H, NH), 6.89 (tt, $^3$J=7.4 Hz, $^4$J=1.1 Hz, 1H, CH), 7.18-7.24 (m, 2H, CH), 7.35-7.42 (m, 2H, CH), 8.52 (s, 1H, NH).

$^{13}$C{$^1$H} NMR (DMSO-d6, 100.61 MHz): δ [ppm]=17.9 (CH$_3$), 38.14 (CH$_2$), 63.9 (CH$_2$), 117.7 (CH), 121.1 (CH), 125.8 (CH$_2$), 128.6 (CH), 135.8 (C$_q$), 140.3 (C$_q$), 155.2 (CO), 166.5 (CO)

Example 2: 2-methyl-2-(3-phenylureido)propyl methacrylate

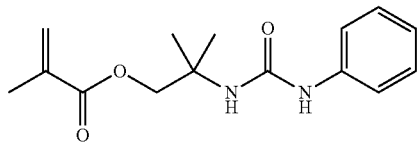 [SMILES: C=C(C)C(=O)OCC(C)(C)NC(=O)Nc1ccccc1]

$^1$H NMR (DMSO-d6, 400.13 MHz): δ [ppm]=1.30 (s, 6H, 2×CH$_3$), 1.90 (s, 3H, CH$_3$), 4.20 (s, 2H, CH$_2$), 5.68 (dq, $^4$J=1.5 Hz, $^2$J=1.1 Hz, 1H, CH), 6.08 (bs, 2H, NH and CH overlapping), 6.88 (tt, $^3$J=7.4 Hz, $^4$J=1.1 Hz, 1H, CH), 7.16-7.24 (m, 2H, CH), 7.30-7.35 (m, 2H, CM, 8.31 (s, 1H, NH).

$^{13}$C{$^1$H} NMR (DMSO-d6, 100.61 MHz): δ [ppm]=17.9 (CH$_3$), 24.4 (CH$_3$), 51.5 (C(CH$_3$)$_2$), 68.8 (OCH$_2$), 117.5 (CH), 120.9 (CCH$_2$), 125.7 (CH), 128.6 (CH), 135.8 (CCH$_2$), 140.3 (Ce), 154.4 (CO), 166.3 (CO).

Example 3: 3-(3-phenylureido)propyl methacrylate

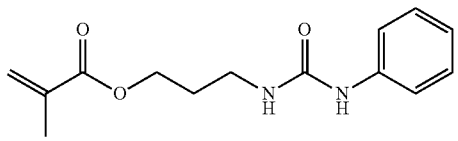 [SMILES: C=C(C)C(=O)OCCCNC(=O)Nc1ccccc1]

$^1$H NMR (DMSO-d6, 400.13 MHz): δ [ppm]=1.78 (q, $^3$J=6.7 Hz, 2H, CH$_2$), 1.89 (bs, 3H, CH$_3$), 3.18 (apparent q, $^3$J=6.6 Hz, 2H, CH$_2$), 4.14 (apparent t, $^3$J=6.4 Hz, 2H, CH$_2$), 5.65 (dq, $^4$J=1.5 Hz, $^4$J=1.1 Hz, 1H, CH$_2$), 6.05 (bs, 1H, CH$_2$), 6.18 (t, $^3$J=5.7 Hz, 1H, NH), 6.88 (tt, $^3$J=7.4 Hz, $^4$J=1.1 Hz, 1H, CH), 7.15-7.24 (m, 2H, CH), 7.34-7.42 (m, 2H, CH), 8.40 (s, 1H, NH).

$^{13}$C{$^1$H} NMR (DMSO-d6, 100.61 MHz): δ [ppm]=17.9 (CH$_3$), 28.9 (CH$_2$), 35.9 (CH$_2$), 62.1 (CH$_2$), 117.7 (CH), 121.0 (CH), 125.6 (CH$_2$), 128.6 (CH), 135.9 (C$_q$), 140.5 (C$_q$), 155.2 (CO), 166.6 (CO)

Example 4: 2-(2-(3-phenylureido)ethoxy)ethyl methacrylate

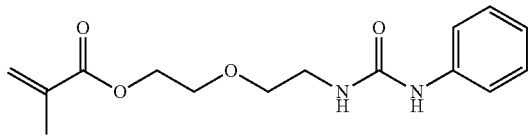 [SMILES: C=C(C)C(=O)OCCOCCNC(=O)Nc1ccccc1]

$^1$H NMR (DMSO-d6, 400.13 MHz): δ [ppm]=1.88 (dd, $^4$J=1.5 Hz, $^4$J=1.0 Hz, 3H, CH$_3$), 3.25 (dt, $^3$J=5.7 Hz, $^3$J=5.5 Hz, 2H, CH$_2$), 3.50 (t, $^3$J=5.5 Hz, 2H, CH$_2$), 3.65-3.69 (m, 2H, CH$_2$), 4.21-4.26 (m, 2H, CH$_2$), 5.65 (dq, $^4$J=1.5 Hz, $^4$J=1.5 Hz, 1H, CH$_2$), 6.02-6.06 (m, 1H, CH$_2$), 6.17 (t, $^3$J=5.7 Hz, 1H, NH), 6.88 (tt, $^3$J=7.4 Hz, $^4$J=1.1 Hz, 1H, CH), 7.17-7.24 (m, 2H, CH), 7.34-7.40 (m, 2H, CH), 8.49 (s, 1H, NH).

$^{13}$C{$^1$H} NMR (DMSO-d6, 100.61 MHz): δ [ppm]=17.9 (CH$_3$), 38.9 (CH$_2$) 63.7 (CH$_2$), 68.0 (CH$_2$), 69.8 (CH$_2$), 117.6 (CH), 120.9 (CH), 125.8 (CH$_2$), 128.6 (CH), 135.8 (C$_q$) 140.5 (C$_q$), 155.2 (CO), 166.5 (CO)

Example 5: 6-(3-phenylureido)hexyl methacrylate

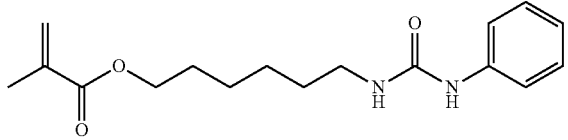 [SMILES: C=C(C)C(=O)OCCCCCCNC(=O)Nc1ccccc1]

$^1$H NMR (DMSO-d6, 400.13 MHz): δ [ppm]=1.24-1.36 (m, 6H, CH$_2$), 1.56-1.68 (m, 2H, CH$_2$), 1.87 (bs, 3H, CH$_3$), 3.07 (dt, 3J=6.7 Hz, $^3$J=5.7 Hz, 2H, CH$_2$), 4.08 (t, $^3$J=6.4 Hz, 2H, CH$_2$), 5.62-5.65 (m, 1H, CH$_2$), 6.01 (bs, 1H, CH$_2$), 6.10 (t, $^3$J=5.5 Hz, 1H, NH), 6.86 (tt, $^3$J=7.2 Hz, $^4$J=1.1 Hz, 1H, CH), 7.16-7.24 (m, 2H, CH), 7.35-7.42 (m, 2H, CH), 8.37 (S, 1H, NH).

$^{13}$C{$^1$H} NMR (DMSO-d6, 100.61 MHz): δ [ppm]=17.9 (CH$_3$), 25.2 (CH$_2$), 26.0 (CH$_2$), 28.1 (CH$_2$), 29.6 (CH$_2$), 38.9 (CH$_2$), 64.2 (CH$_2$), 117.6 (CH), 120.8 (CH), 125.4 (CH), 128.6 (CH), 136.0 (C$_q$), 140.6 (C$_q$), 155.2 (CO), 166.6 (CO).

Example 6: 6-(3-cyclohexylureido)hexyl methacrylate

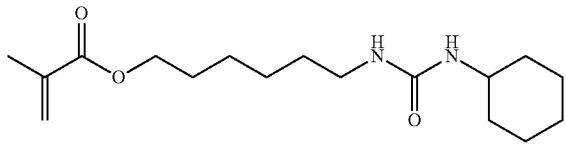 [SMILES: C=C(C)C(=O)OCCCCCCNC(=O)NC1CCCCC1]

6-Aminohexanol (0.40 mol, 1.00 eq.) methyl methacrylate (602 g, 6.02 mol, 15 eq.) and MEHQ (0.02 g, 200 ppm rel. to product) are weighed into a reactor with mechanical stirring, air supply, sump temperature display, a filling element column set on it, as well as an automatically controlled column head with reflux and distillate cooler. The mixture is cooled to 9° C. and cyclohexyl isocyanate (49.76 g, 0.398 mol, 0.99 eq., 50 wt. % in methyl methacrylate) is added within 20 minutes, so that the temperature does not exceed 20° C. After complete addition, the mixture is stirred for additional 30 minutes, thereby brought to room temperature and then heated to 100° C. to remove any water as water-methyl methacrylate azeotrope. The mixture is cooled to 80° C., the catalyst IPT (0.96 g, 1% based on intermediate alcohol), and methyl methacrylate (35 g, azeotrope loss) are added. Again, the mixture is heated to boiling, and the resulting methyl methacrylate-methanol azeotrope is distilled off at a reflux ratio of 2:1, up to a maximum head temperature of 75° C., and later at a reflux ratio of 10:1, until a constant column head temperature of 98-101° C. is reached. The mixture is cooled down to 80° C., and diluted sulfuric acid (3.84 g) is added, followed by sodium carbonate (5.76 g). The mixture is filtered, and the product is obtained upon cooling of the mother liquor as a colourless precipitate, which is filtered off and dried. Yield: 115.7 g (94%).

$^1$H NMR (DMSO-d6, 400.13 MHz): δ [ppm]=0.96-1.17 (m, 3H, CH$_2$), 1.18-1.40 (m, 8H, CH$_2$), 1.45-1.55 (m, 1H, CH$_2$), 1.56-1.67 (m, 4H, CH$_2$), 1.67-1.77 (m, 2H, CH$_2$), 1.87 (s, 3H, CH$_3$), 2.95 (dt, $^3$J=6.7 Hz, $^3$J=6.3 Hz, 2H, CH$_2$), 3.26-3.40 (m, 1H, CH), 4.07 (t, $^3$J=6.8 Hz, 2H, CH$_2$), 5.56-5.70 (m, 3H, CCH$_2$ and NH), 6.00 (s, 1H, NH).

$^{13}$C{$^1$H} NMR (DMSO-d6, 100.61 MHz): δ [ppm]=17.9 (CH$_3$), 24.4 (CH$_2$), 25.2 (CH$_2$), 25.3 (CH$_2$), 26.0 (CH$_2$), 28.0 (CH$_2$), 29.9 (CH$_2$), 33.3 (CH$_2$), 39.0 (CH$_2$NH), 47.6 (CH), 64.1 (CH$_2$O), 125.3 (CH$_2$), 135.9 (CCH$_2$), 157.3 (CO), 166.5 (CO).

The invention claimed is:

1. A one pot process for preparing at least one (meth)acrylate of the general formula (I)

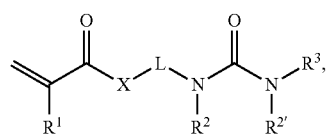

wherein
R$^1$ is selected from the group consisting of —H and -Me;
R$^2$ is selected from the group consisting of —H and a C$_1$-C$_{20}$ linear, branched or cyclic alkyl or aryl group;
R$^{2'}$ is —H;
R$^3$ is selected from the group consisting of —H; a C$_1$-C$_{20}$ linear, branched or cyclic alkyl or aryl group; benzene-sulfonyl; tosyl; p-chlorophenyl; adamantyl; 2,6-dimethyl phenyl; 3,5-dimethyl phenyl; and 2,6-dipropyl phenyl;
R$^2$ and R$^3$ are the same or different;
X is selected from the group consisting of —O— and —NH—; and
L is a C$_2$-C$_{20}$ linear, branched or cyclic alkyl or aryl group, in which optionally, one or more carbon atoms within the carbon chain is replaced by one or more —O—, —NH— or —S— heteroatoms, the process comprising:
reacting, in an initial reaction phase, an aminoalcohol or diamine of the general formula (V)

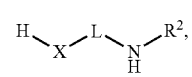

wherein X, R$^2$, L are as defined above,
with an isocyanate of the general formula (VI)

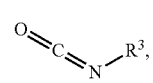

wherein R$^3$ is as defined above,
in the presence of a reactive diluent of the general formula (III)

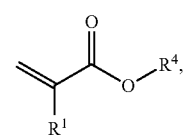

wherein R$^4$ is C$_1$ to C$_4$ alkyl,
to obtain, in situ, an intermediate compound of the general formula (II)

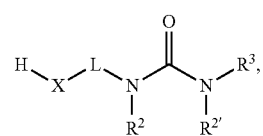

wherein X, R$^2$, R$^{2'}$, R$^3$, L are as defined above; and
immediately reacting, in a second reaction phase, the intermediate compound with the reactive diluent, to form the at least one (meth)acrylate.

2. The process according to claim 1, wherein
R$^1$ is methyl,
R$^2$ is selected from the group consisting of hydrogen and a C$_1$ to C$_8$ linear or branched alkyl,
R$^3$ is selected from the group consisting of methyl, ethyl, propyl, isopropyl, butyl, ethyl hexyl, cyclohexyl, and phenyl,
X is oxygen; and L is selected from the group consisting of ethyl, propyl, butyl, pentyl, hexyl, heptyl, octyl, and ethoxyethyl.

3. The process according to claim 1, wherein the process is carried out in the presence of at least one catalyst selected from the group consisting of $Zr(acac)_2$, LiOH, CaO, dioctyltin oxide, dibutyltin laurate, titanium isopropoxide, and a combination thereof.

4. The process according to claim 1, wherein the process is carried out in the presence of at least one catalyst selected from the group consisting of titanium isopropoxide, CaO/LiOH, CaO/LiCl, dioctyltin oxide, and dibutyltin laurate.

5. The process according to claim 3, wherein the at least one catalyst is present in an amount of between 0.01 and 5 wt. %, based on an amount of the aminoalcohol or diamine.

6. The process according to claim 1, wherein the reaction temperature in the initial reaction phase is kept between 0° C. and 80° C.

7. The process according to claim 1, wherein the reaction temperature in the second reaction phase is kept between 30° C. and 180° C.

8. The process according to claim 1, wherein the reactive diluent is at least one alkyl (meth)acrylate selected from the group consisting of propyl (meth)acrylate, ethyl (meth)acrylate, i-propyl (meth)acrylate, i-butyl (meth)acrylate, n-butyl (meth)acrylate, and methyl (meth)acrylate.

9. The process according to claim 1, wherein the reactive diluent is methyl(meth)acrylate.

10. The process according to claim 1, wherein an amount of reactive diluent used is between 1 and 50 moles per mole of the aminoalcohol or diamine.

11. The process according to claim 1, wherein an amount of the isocyanate is 0.80 to 1.20 eq. per eq. of the aminoalcohol or diamine.

12. The process according to claim 1, wherein the process is carried out in the presence of at least one polymerization inhibitor selected from the group consisting of hydrochinone monomethyl ether, 2,4-dimethyl-6-tert-butylphenol, 2,6-di-tert-butyl-4-methyl-phenol, octadecyl-3-(3,5-di-tert-butyl-4-hydroxyphenyl)-propionate, 4-hydroxy-2,2,6,6-tetramethylpiperidin-1-oxyl, and a mixture thereof.

13. The process according to claim 12, wherein the at least one polymerization inhibitor is hydrochinone monomethyl ether.

14. The process according to claim 12, wherein an amount of the at least one polymerization inhibitor at the beginning of the process is adjusted to between 0 and 5,000 ppm, based on an amount of theoretically expected product at full conversion.

15. The process according to claim 1, wherein the at least one (meth)acrylate is obtained via precipitation.

16. The process according to claim 6, wherein the reaction temperature in the initial reaction phase is kept between 0° C. and 30° C.

17. The process according to claim 7, wherein the reaction temperature in the second reaction phase is kept between 80° C. and 130° C.

18. The process according to claim 10, wherein the amount of reactive diluent used is between 3 and 10 moles per mole of the aminoalcohol or diamine.

19. The process according to claim 11, wherein the amount of the isocyanate is 0.95 to 1.05 eq. per eq. of the aminoalcohol or diamine.

20. The process according to claim 12, wherein the at least one (meth)acrylate is obtained via precipitation, and wherein the at least one polymerization inhibitor is co-precipitated with the at least one (meth)acrylate.

* * * * *